United States Patent [19]

Olesen et al.

[11] Plant 4,941

[45] Nov. 16, 1982

[54] ROSE PLANT

[76] Inventors: Pernille Olesen; Mogens Olesen, both of 58 Kelleriisvej, DK 3490 Kvistgaard, Denmark

[21] Appl. No.: 278,186

[22] Filed: Jun. 29, 1981

[51] Int. Cl.[3] ..... A01H 5/00

[52] U.S. Cl. ..... Plt./12

[58] Field of Search ..... Plt./12

*Primary Examiner*—James R. Feyrer

*Attorney, Agent, or Firm*—Vincent G. Gioia

[57] ABSTRACT

A new hybrid tea rose variety of current red and silver bicoloring.

1 Drawing Figure

The present invention relates to a new and distinct variety of rose plant of the hybrid tea rose class, which was originated by my crossing as seed and pollen parents, two unnamed, unpatented seedlings of my creation.

Among the novel characteristics possessed by this new variety which distinguish it from its parents and all other varieties of which I am aware are large bicolored flowers of current red petal top surface and silver to pale yellow petal undersurface and good exhibition, high centered form. The flower's unique coloring effect is discernible even upon aging because the center petals remain erect. Flowers are resistant to fading and are long lasting on the plant and as a cut flower. The plant is tall growing and vigorous and particularly hardy for a bicolor. Asexual reproduction by budding of the new variety as performed in Clackamas County, Oreg., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "11B" is plate 11B of the Royal Horticultural Society Color Chart.

Parentage: Seedling.

*Seed parent.*—Unnamed seedling.

*Pollen parent.*—Unnamed seedling.

Class: Hybrid tea.

The following observations are made of specimens grown outdoors in Clackamas County, Oreg. during the month of October.

FLOWER

Blooming habit: Continuous.

A. Bud:

(1) *Size.*—Large.

(2) *Form.*—High centered.

(3) *Color.*—Long sepals divide to reveal a large bud of red coloring but soon display the silver toned petal undersurface with 11B to 11D shading and some pink tones.

(4) *Sepals.*—Long, fancy.

(5) *Peduncle.*—Length — long. Aspect — straight. Strength — erect, strong. Color — near 144C.

B. Bloom:

(1) *Size.*—Average size when fully expanded — about 5½ to 6 inches.

(2) *Borne.*—Singly, rarely with side buds.

(3) *Form.*—High centered, rolling slightly outward but retaining classic form.

(4) *Petalage.*—Number of petals under normal conditions — about 45 to 50.

(5) *Color.*—Heavy petalled flowers open slowly displaying warm red 46A petal top surface which quill to points in sharp contrast to light colored petal undersurface which appears silvery yellow with darker yellow at point of petal attachment and pink tones at petal edge. Coloring as described is resistant to fading upon aging.

C. Petals:

(1) *Texture.*—Thick.

(2) *Appearance.*—Velvety inside, flat reverse.

(3) *Form.*—Deltoid.

(4) *Arrangement.*—Regular, spiral opening.

(5) *Petaloids in center.*—Many, large.

(6) *Persistence.*—Drop off cleanly.

(7) *Fragrance.*—Strong, old rose.

(8) *Lasting quality.*—Long lasting on plant and as cut flower.

REPRODUCTIVE ORGANS

A. Stamens, filaments and anthers:

(1) *Arrangement.*—Numerous, outer stamens longer.

(2) *Color.*—Filament 45C, anthers 12C.

B. Pollen:

*Color.*—14B.

C. Styles: Many, uneven, short, hairy.

*Color.*—2B.

D. Stigmas:

*Color.*—7C.

E. Hips: None observed.

PLANT

A. Form: Upright, slightly spreading.

B. Growth: Tall, vigorous, long stemmed.

*Height attained.*—About 5½ to 6 feet.

C. Foliage: Compound 5 leaflets.

(1) *Size.*—Large.

(2) *Quantity.*—Abundant, close set.

(3) *Color.*—New foliage: Upper side — near 178A. Under side — near 180A. Old foliage: Upper side — near 137B. Under side — near 138B.

(4) *Shape.*—Oval.

(5) *Texture.*—Upper side is leathery and shiny, under side is flat, dull.

(6) *Edge.*—Serrate.

(7) *Serration.*—Double.

(8) *Leaf stem.*—Color — near 144A. Under side — near 151C.

(9) *Stipules.*—Long, pointed, minutely serrate.

(10) *Resistance to disease.*—Blackspot — good. Mildew — excellent. Rust — good.

D. Wood:

(1) *New wood.*—Color — near 144B. Bark — smooth.

(2) *Old wood.*—Color — near 148C. Bark — smooth.

E. Thorns:

(1) *Thorns.*—Quantity (main stalk): ordinary, large. On laterals from stalk — few. Form — strongly recurved. Length — large. Color — near 39A. Position — irregular.

(2) *Prickles.*—Few.

F. Winter hardiness: Good winter hardiness.

I claim:

1. A new and distinct variety of rose plant of the hybrid tea class, substantially as shown and described, characterized particularly by flowers of unusual red and silvery yellow bicoloring resistant to fading upon aging.

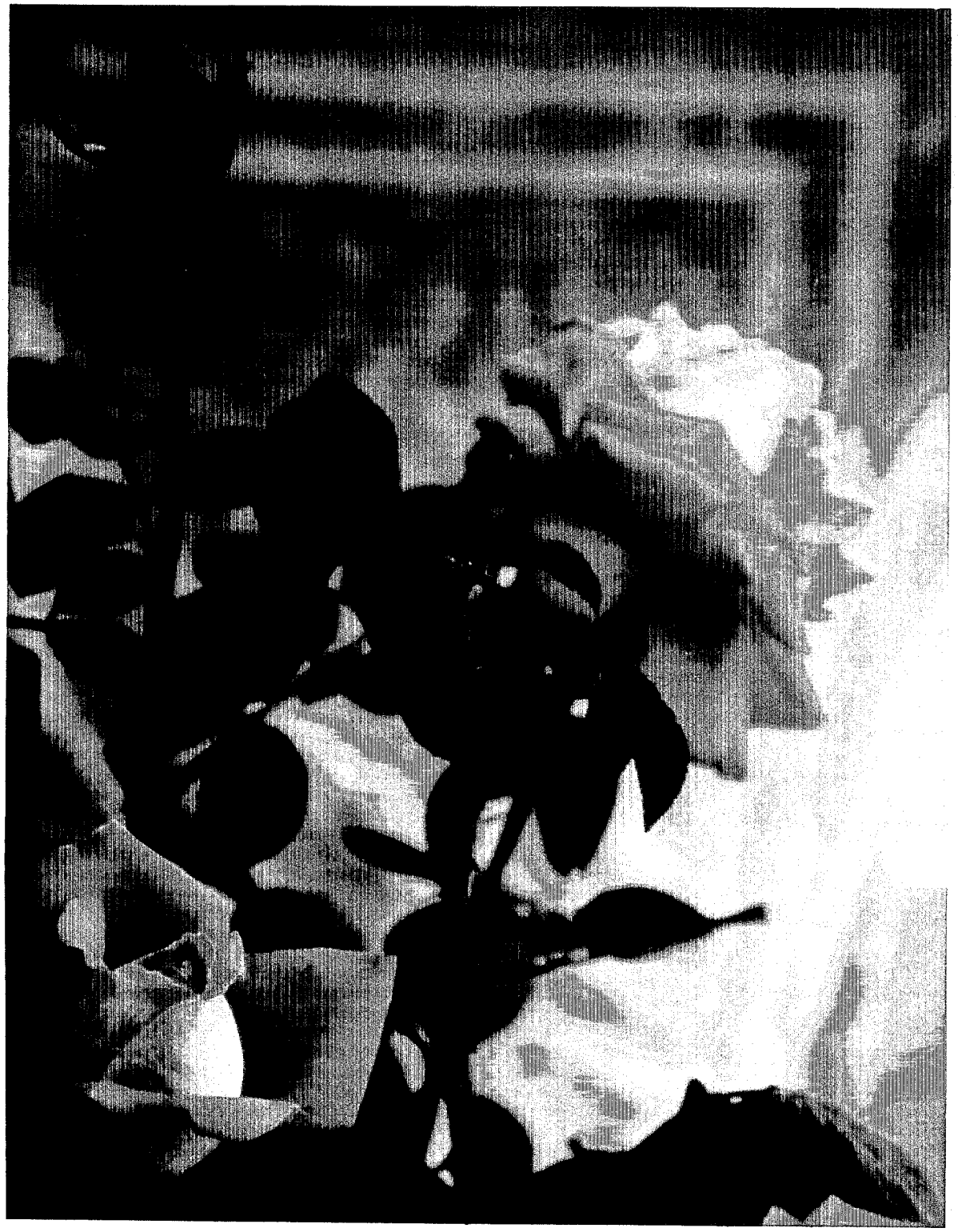

* * * * *